(12) United States Patent
Lechot et al.

(10) Patent No.: US 7,637,909 B2
(45) Date of Patent: Dec. 29, 2009

(54) REAMER SPINDLE FOR MINIMALLY INVASIVE JOINT SURGERY

(75) Inventors: André Lechot, Orvin (CH); Yves Desarzens, Corgémont (CH); Hugh Davies, Lignières (CH); Patrick White, West Chester, PA (US)

(73) Assignee: Greatbatch Medical S.A., Clarence, NY (US)

( * ) Notice: Subject to any disclaimer, the term of this patent is extended or adjusted under 35 U.S.C. 154(b) by 328 days.

(21) Appl. No.: 11/123,932

(22) Filed: May 5, 2005

(65) Prior Publication Data

US 2005/0216022 A1    Sep. 29, 2005

Related U.S. Application Data (63) Continuation-in-part of application No. 10/510,384, filed as application No. PCT/IB03/01725 on Apr. 28, 2003.

(60) Provisional application No. 60/376,479, filed on Apr. 30, 2002, provisional application No. 60/384,186, filed on May 30, 2002, provisional application No. 60/459,594, filed on Apr. 2, 2003.

(51) Int. Cl.
*A61B 17/00* (2006.01)
*A61B 17/58* (2006.01)

(52) U.S. Cl. .............................. 606/80; 606/81; 606/96

(58) Field of Classification Search .................. 606/80, 606/81, 82, 91, 99, 100, 180, 96; 623/22.21, 623/22.39; 403/349, 348; 408/93, 104, 94; 279/93, 145, 89, 94, 104, 143
See application file for complete search history.

(56) References Cited

U.S. PATENT DOCUMENTS 4,305,394 A * 12/1981 Bertuch, Jr. .................. 606/91

(Continued)

FOREIGN PATENT DOCUMENTS

JP    05 123334 A    5/1993

(Continued)

OTHER PUBLICATIONS

Biomet, Inc.: Biomet, Inc. Catalog, published in the late 1980s in the U.S., p. B-2 seems to disclose a curved inpactor shaft (No. 424485) for use in hip replacement surgeries.

(Continued)

*Primary Examiner*—Pedro Philogene
(74) *Attorney, Agent, or Firm*—Michael F. Scalise (57) ABSTRACT

An adjustable reamer spindle is provided to aid the surgeon in controlling the instrument. The reamer spindle is easily disassembled for cleaning. The spindle has a repositionable handle, a locking ring, and an elastic device. The elastic device biases against a handle locking mechanism that locks the repositionable handle at angular positions about an axis of the spindle. The elastic device further biases a locking ring into a locked position. The locking ring aids in holding the reamer spindle together. Removal of the locking ring against an elastic bias of the elastic means unfastens an end of the assembly in order to facilitate disassembly and/or cleaning. Adjustment of the position of the handle about the spindle enables the palm/grip of each hand to be changed in order to provide maximum control in different orientations. The adjustment is desirable in order to accommodate operating on the left or right side of the patient, standing behind or in-front of the patient, or the use of a different surgical approach. Further, adjustment is important to accommodate the differing needs of surgeons who are naturally left or right handed.

31 Claims, 12 Drawing Sheets

U.S. PATENT DOCUMENTS

| | | | |
|---|---|---|---|
| 4,528,980 | A | 7/1985 | Kena |
| 5,171,312 | A | 12/1992 | Salyer |
| 5,176,711 | A | 1/1993 | Grimes |
| 5,474,560 | A | 12/1995 | Rohr, Jr. |
| 5,925,077 | A * | 7/1999 | Williamson et al. ...... 623/22.34 |
| 5,951,561 | A * | 9/1999 | Pepper et al. .................. 606/80 |
| 6,174,313 | B1 | 1/2001 | Bonutti |
| 6,312,438 | B1 | 11/2001 | Adams |
| 6,436,107 | B1 * | 8/2002 | Wang et al. .................. 606/139 |
| 6,451,058 | B2 | 9/2002 | Tuke |
| 6,475,221 | B1 | 11/2002 | White |
| 6,676,706 | B1 | 1/2004 | Mears |
| 6,854,742 | B2 * | 2/2005 | Salyer et al. .................. 279/93 |
| 7,008,430 | B2 * | 3/2006 | Dong et al. .................... 606/80 |
| 2003/0050645 | A1 | 3/2003 | Myers et al. |
| 2003/0130741 | A1 | 7/2003 | McMinn |
| 2004/0087958 | A1 * | 5/2004 | Myers et al. .................. 606/80 |

FOREIGN PATENT DOCUMENTS

| | | | |
|---|---|---|---|
| JP | 05123334 | | 5/1993 |
| WO | PCT/GB03/00557 | | 8/2003 |
| WO | WO 03/065906 | * | 8/2003 |
| WO | WO 03/065906 A2 | | 8/2003 |
| WO | WO 03/065906 A3 | | 8/2003 |
| WO | WO 03092513 | | 11/2003 |

OTHER PUBLICATIONS

Aug. 14, 2003, PCT International Search Report PCT/GB03/00557.

May 11, 2004, PCT International Preliminary Exam Report PCT/GB03/00557.

Nov. 13, 2006, Affidavit Under 37 CFR 1.131 filed with the USPTO Nov. 13, 2006 during prosecution of U.S. Appl. No:10/284,003, now USP 7,326,215.

May 12, 2004 International Preliminary Examination Report and International Search Report PCT/GB03/00557.

Aug. 20, 2008 Response to Official Communication filed in EP 03706689.1.

Mar. 3, 2006 English translation of notification of first office action in China application 038061899.

Affidavit Under 37 CFR 1.131 filed with the USPTO Mar. 28, 2005 during prosecution of U.S. Appl. No.10/284,003, now USP 7,326,215.

Amendment showing claims pending in 10503788 naming Channa as inventor.

Application 11/122,092, as filed, naming Channa, as inventor.

Second Preliminary Amendment showing claims, in 11/122,092.

Suggestion for interference filed in application 11/122,092, on Feb. 24, 2006.

Suggestion for interference filed in application 11/122,092, on Mar. 10, 2006.

Office action dated Jul. 9, 2008 in application 10/503,788.

Office action dated Mar. 12, 2009 in application 10/503,788.

Office action dated Dec. 17, 2007 in application 10/503,788.

* cited by examiner

REAMER SPINDLE FOR MINIMALLY INVASIVE JOINT SURGERY

CROSS REFERENCE TO RELATED APPLICATIONS

This application is a continuation-in-part of application Ser. No. 10/510,384, filed 5 Oct. 2004, which is a national stage entry of international application no. PCT/IB03/01725, filed 28 Apr. 2003, and PCT/IB03/01725 claims the benefit of U.S. Provisional Application 60/376,479, filed 30 Apr. 2002; and U.S. Provisional Application 60/384,186, filed 30 May 2002; and U.S. Provisional Application 60/459,594, filed 2 Apr. 2003, the contents of all of which are incorporated herein by reference and relied upon.

BACKGROUND OF THE INVENTION

This invention relates to handles for reamers, and, more particularly, to adjustable handles for acetabular reamers that can be easily sterilized.

Complicated mechanical devices have crevasses and recesses that are difficult, if not almost impossible, to clean with ease. Devices that are not properly cleaned and sterilized contribute to the risk of disease transfer from patient to patient following the emergence of certain "prions" that are not killed by normal hospital sterilisation and need to be physically removed by washing/rinsing.

In GB PCT application no GB0202934A to Chana, entitled, Improved Surgical Devices and Methods of Use, the contents of which are incorporated by reference hereto, several reamer spindle designs are discussed. However, none includes a handle having the ability to be angularly repositioned about the axis of the housing and none uses a single spring to both lock the angularly repositionable handle in place and to lock the two housing portions in place.

What is needed therefore is a reamer spindle that is easily adjustable, disassemblable, and cleanable and which includes an easily repositionable handle using a mechanism requiring few components.

SUMMARY OF THE INVENTION

An adjustable reamer spindle is provided to aid the surgeon in controlling the instrument. Adjustment of the position of the handle axis of the spindle enables the axis through the palm/grip of each hand to change in order to provide maximum control in different orientations. The adjustment is desirable in order to accommodate operating on the left or right side of the patient, standing behind or in-front of the patient, or the use of a different surgical approach. Further, adjustment is important to accommodate the differing needs of surgeons who are naturally left or right handed. Thus, the comfort for holding and using the instrument is enhanced through adjustment.

In an objective of the invention, the handle can be easily cleaned, in that the design access to all surfaces such that they can be cleaned (i.e., one part covering another can be moved or removed to expose all surfaces). Further, the design enables the reduction in number of small radius internal corners, crevasses and small gaps and the absence of blind holes.

In another objective, a reamer handle is provided that is easy to disassemble and for which the disassembly is easy to learn.

In another object, the invention minimises the number of pieces and thus the risk that any individual part might be lost.

BRIEF DESCRIPTION OF DRAWINGS

The attached drawings represent, by way of example, different embodiments of the subject of the invention.

DETAILED DESCRIPTION

Figure 1:
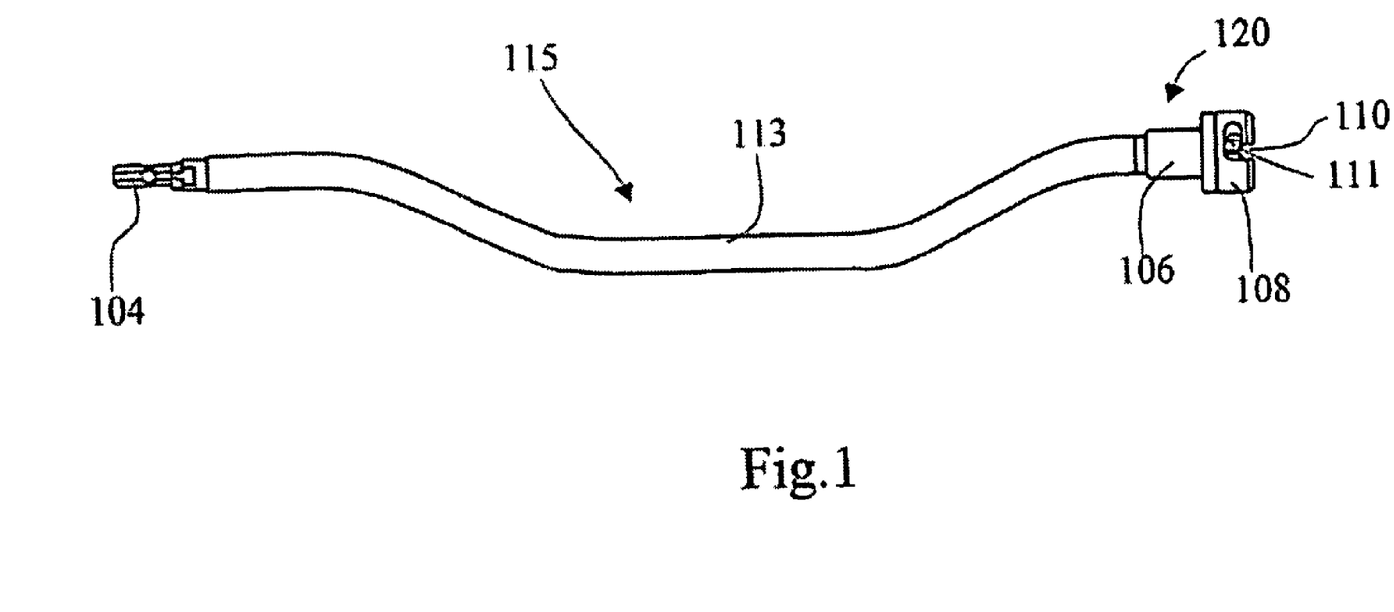
FIG. 1 is a side view of the reamer spindle of the present invention.
Figure 2:
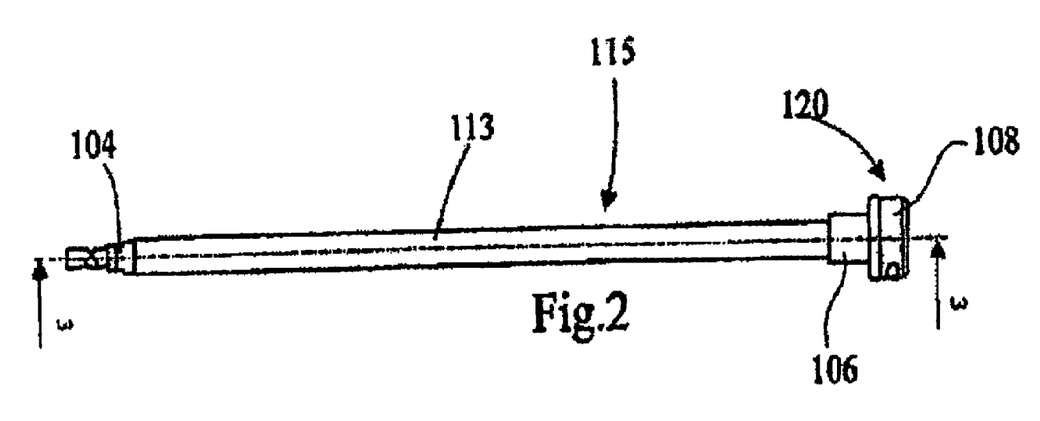
FIG. 2 is a top view of the reamer spindle of the present invention.
Figure 3:
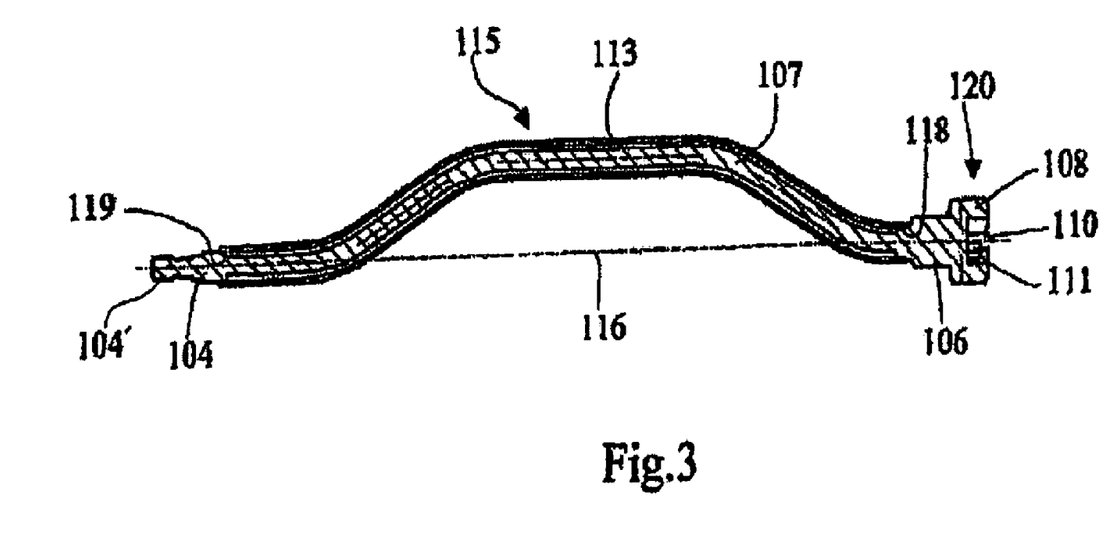
FIG. 3 is a section view taken along line 3-3 shown in FIG. 2.
Figure 4:
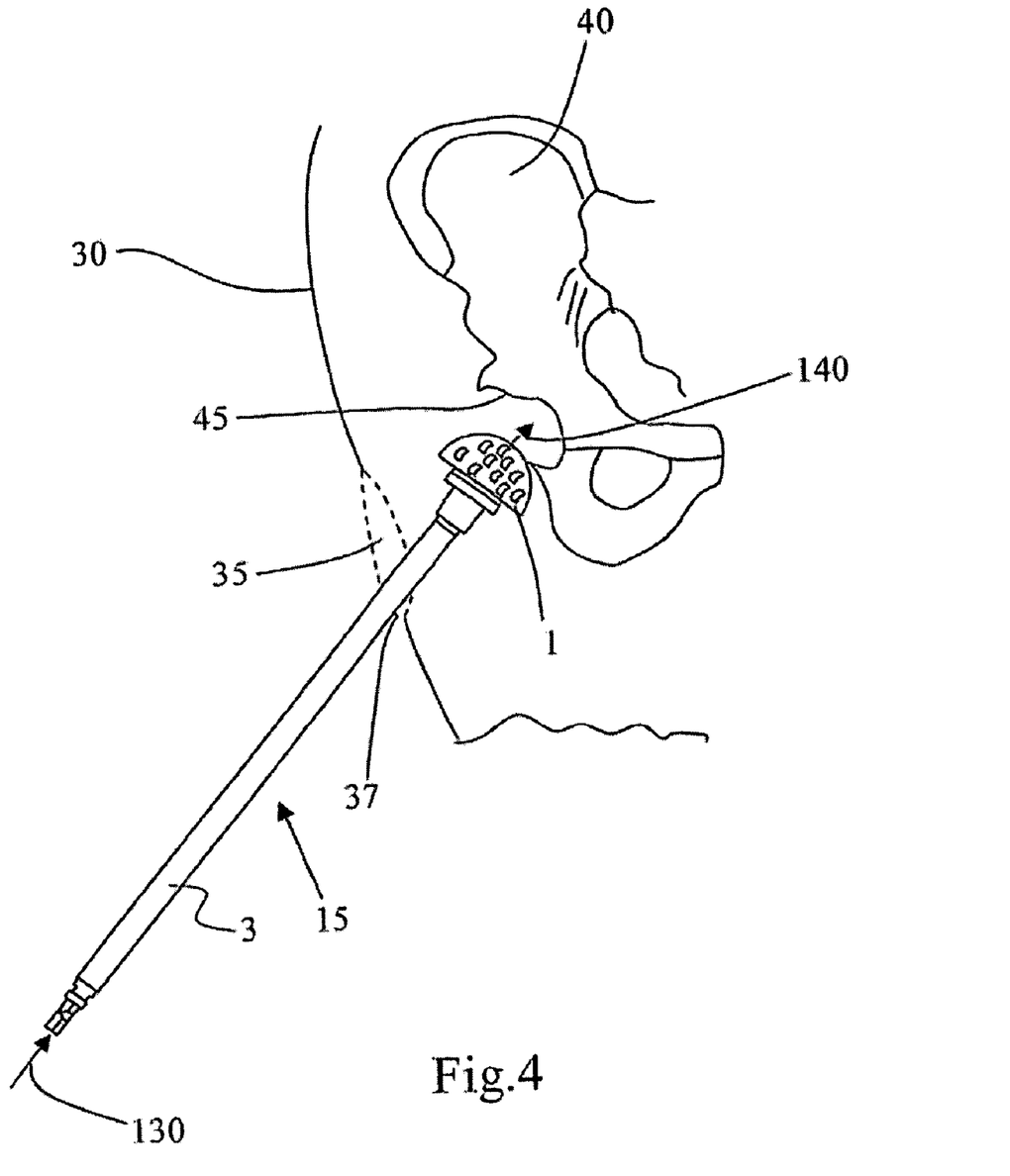
FIG. 4 is a plan view showing a traditional reamer spindle of the prior art being used in a minimally invasive approach for reaming the acetabular socket.
Figure 5:
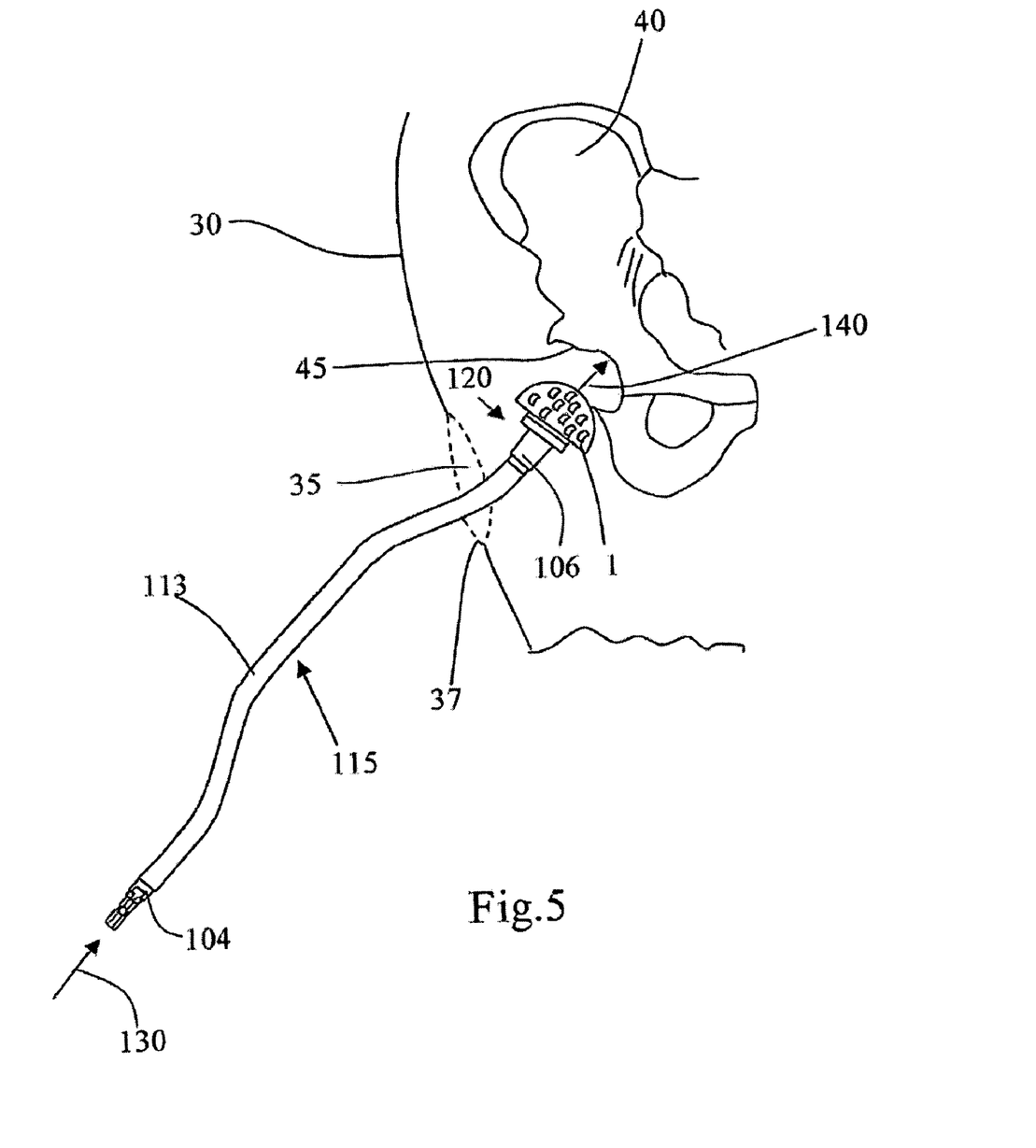
FIG. 5 is a plan view showing the reamer spindle of the present invention being used in a minimally invasive approach for reaming the acetabular socket.

The reamer spindle 115 shown in FIGS. 1-3, and 5 consists of a drive fitting 104, which is adapted to be joined to a rotary power source used to drive the shaft 107 of the reamer spindle 115. The shaft 107 is mounted to a reamer holding mechanism 120. The reamer holding mechanism 120 can be selected from a variety of mechanisms useful for capturing and holding a surgical reamer 1 during an orthopedic surgical procedure. It is clear that many different mechanisms exist which would be useful for this task, however the present inventors have selected the preferred bayonet style mechanism 120 for purpose of example. The reamer holding mechanism 120 comprises a slide 106 carrying a pin component 111 of the reamer holding mechanism 120. The pin 111 works cooperatively with the catch 110 located in the head 108 to form the bayonet for capturing different size reamers 1 while allowing their easy release for size interchangeability and cleaning. The reamers 1 selected for use with the reamer spindle 115 can be shaped and sized for cutting different osseous sites within the body. It is widely known that reamers can be designed to cut the patella in a knee or the glenoid in a shoulder or the socket 45 in an acetabulum 40 as shown in FIGS. 4-5.

Referring to FIGS. 4-5, the reamer spindle 115 of the present invention and the spindle 15 of the prior art invention are shown passing through a miniature incision 35 in the patient's skin 30. In FIG. 4, the reamer spindle 15 is shown approaching the acetabulum 40 in a preferred orientation for reaming the socket 45. The difficulty with the prior art spindle 15 is shown as the shaft 3 impinges on the miniature incision 35 at edge of the incision 37. The current surgical protocols are being pushed to the limits and the incision sizes are being reduced in the hopes of increasing the patient's speed to recovery. In some cases surgeons are using a two-incision approach, one to reach the acetabulum and the other to reach the femur. Depending on the situation, either the one incision or the two incision technique results in less trauma to the patient, thus requiring the instruments to be flexible and more optimally designed to make up for the lack of operating space.

The reamer 115 of FIG. 5 shows a new reamer spindle 115, which has a bent housing 113 containing the drive shaft 107. The drive shaft 107 can be selected from a variety of current torque transmitting mechanisms or devices including a Nickel Titanium shaft, a flexible round or flat wire wound cable, a series of gear driven shafts, or a series of shafts interconnected by universal joints. The drive shaft 107 can also be selected from any torque transmission mechanism or device deemed appropriate for the application. The drive shaft 107 can be held to the housing 113 with an optional series of bearings 118-119 which keep the drive shafts from bearing against/riding on the inside of the housing 113 and act as a shield to protect the inner housing from blood. Other means for holding the shaft to the housing would be acceptable. The most important feature of the drive shaft 107 is that it conforms to the selected housing 113 and sufficiently supplies torque to the cutter 1.

Figure 8:
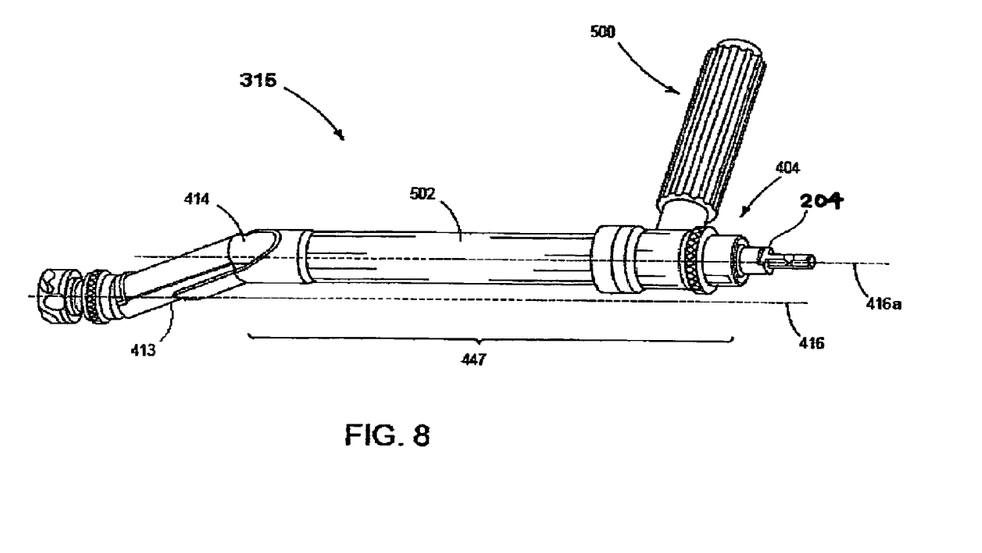
FIG. 8 is a perspective view of an alternate embodiment of the invention having a repositionable handle.

The housing 113 is formed from cannulated material and the drive end 104 is substantially collinear with the holding mechanism 120 along axis 116. Referring now to FIGS. 8 et seq., alternatively, the drive end 104 could be situated along an axis parallel or offset to axis 116. The bends in the housing are optimally placed at critical locations to pass through the miniature incision without impinging on the skin 30 at location 37 while still maintaining the same surgical protocol. The drive end 104 and the holding mechanism 120 should be in line or on parallel axes so that the applied force 130 results in an axial motion 140. This allows the surgeon to maintain the existing technique because inherently reamer spindle 15 in FIG. 4 would give the same result since it has a straight drive shaft 3. Thus, the surgeon is allowed to apply a load directly along the path of reaming.

Figure 6:
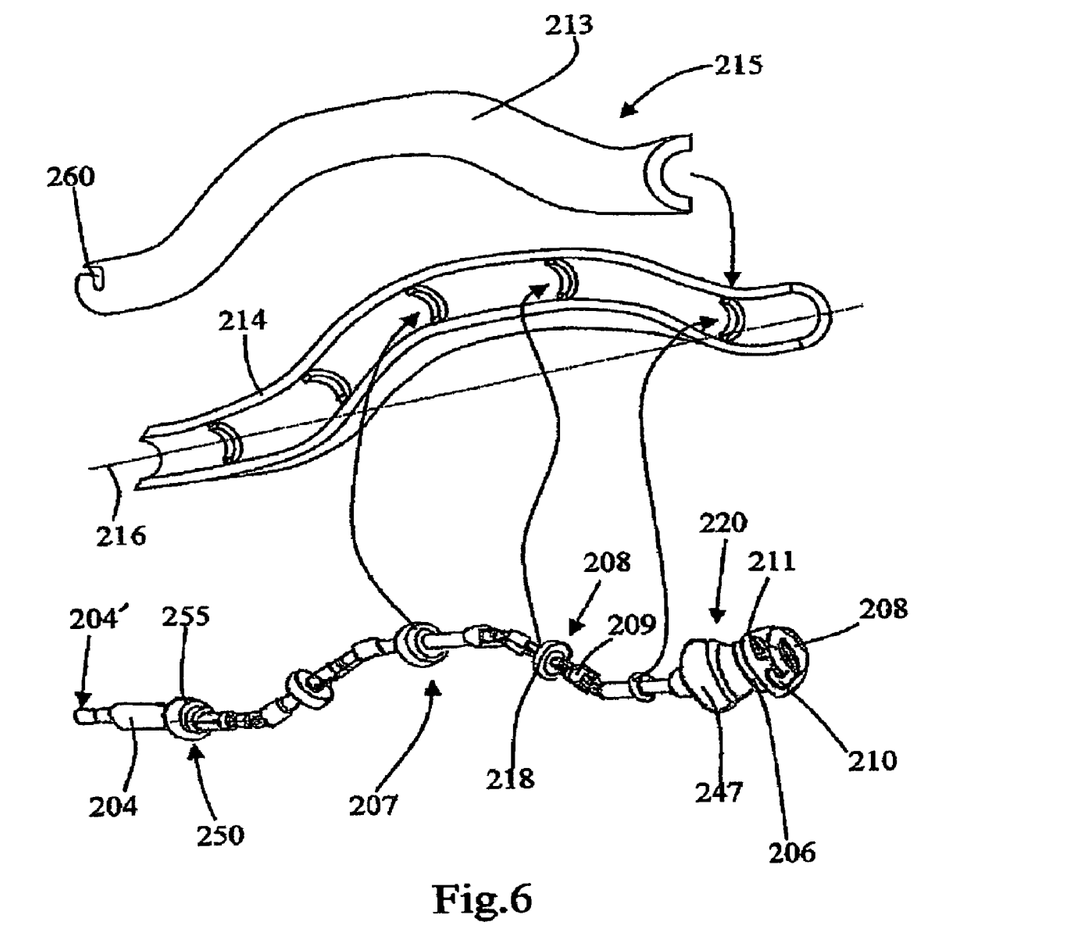
FIG. 6 is an exploded assembly of an alternative embodiment of the present invention.

Referring now to FIG. 6, an alternative embodiment is shown. Similar to FIGS. 1-3 and 5, the reamer spindle 215 has a drive fitting 204, which is adapted to be joined to a rotary power source used to drive the shaft 207 of the reamer spindle 215. The drive shaft 207 can be selected from a variety of current torque transmitting mechanisms or devices including a Nickel Titanium shaft, a flexible round or flat wire wound cable, a series of gear driven shafts, or a series of linkages 208 interconnected by universal joints 209. The drive shaft 207 can also be selected from any torque transmission mechanism or device deemed appropriate for the application. In this embodiment, the shaft 207 is constructed from a series of linkages 208 containing universal joints 209 and bearing members 218 which rest against collars 218' in the housing members 213, 214.

The reamer holding mechanism 220 is preferably a bayonet fitting with a slide 206 carrying a pin component 211 of the reamer holding mechanism 220. The pin 211 works cooperatively with the catch 210 located in the head 208 to form the bayonet for capturing different size reamers while allowing their easy release for size interchangeability and cleaning. The drive shaft 207 is set in housing members 213 and 214, which are separable for cleaning.

Figure 7:
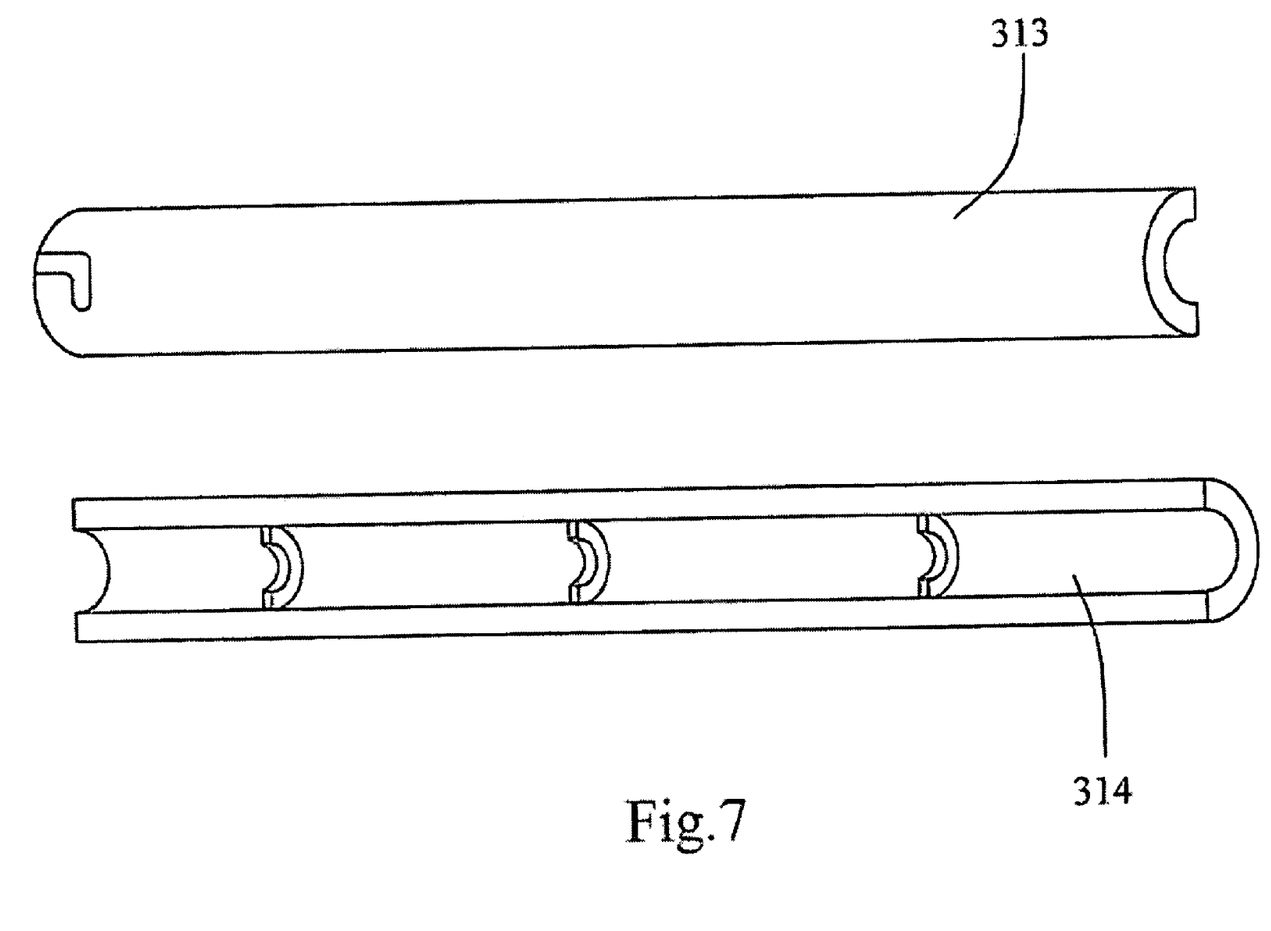
FIG. 7 is an alternative shape housing of the alternative embodiment shown in FIG. 6

There are many ways of connecting the housing members 213 and 214 together. For example, the shaft 207 can include a capture mechanism 247 which is adapted to receive the front ends of the housing members 213 and 214 aligning each with one another and encapsulating the drive shaft 107 to protect the patient's skin from contacting the torque transmitting shaft 207 during operation. Once the housing members 213 and 214 are aligned, a locking mechanism 250 comprised of a ring 255 and a catch 260, which is located in the housing member 213, interact with one another to retain the housing members 213 and 214 in a closed fashion. As with the embodiment described in FIGS. 1-3, and 5, it is preferable to have the drive end 204 substantially collinear with the holding mechanism 220 along axis 216. The housing members 213 and 214 are shown preferably in a bent configuration; however, the reamer spindle 215 with a separable housing includes the option of a straight configuration, as is the case with housing members 313 and 314, shown in FIG. 7, having no bend.

Referring now to FIG. 8, in another embodiment 315, the drive end 404 is situated along an axis parallel and offset to axis 416. Further, a repositionable handle 500 doubles as a component of the capture mechanism 447 in order to hold the two housing members 413 and 414 together.

The capture mechanism 447 slides over the front ends 448 of the housing members 413 and 414, aligning each with one another and thus encapsulating the drive shaft 107 in order to protect the patient's skin from contacting the torque transmitting shaft 107 after being assembled.

Figure 9A:
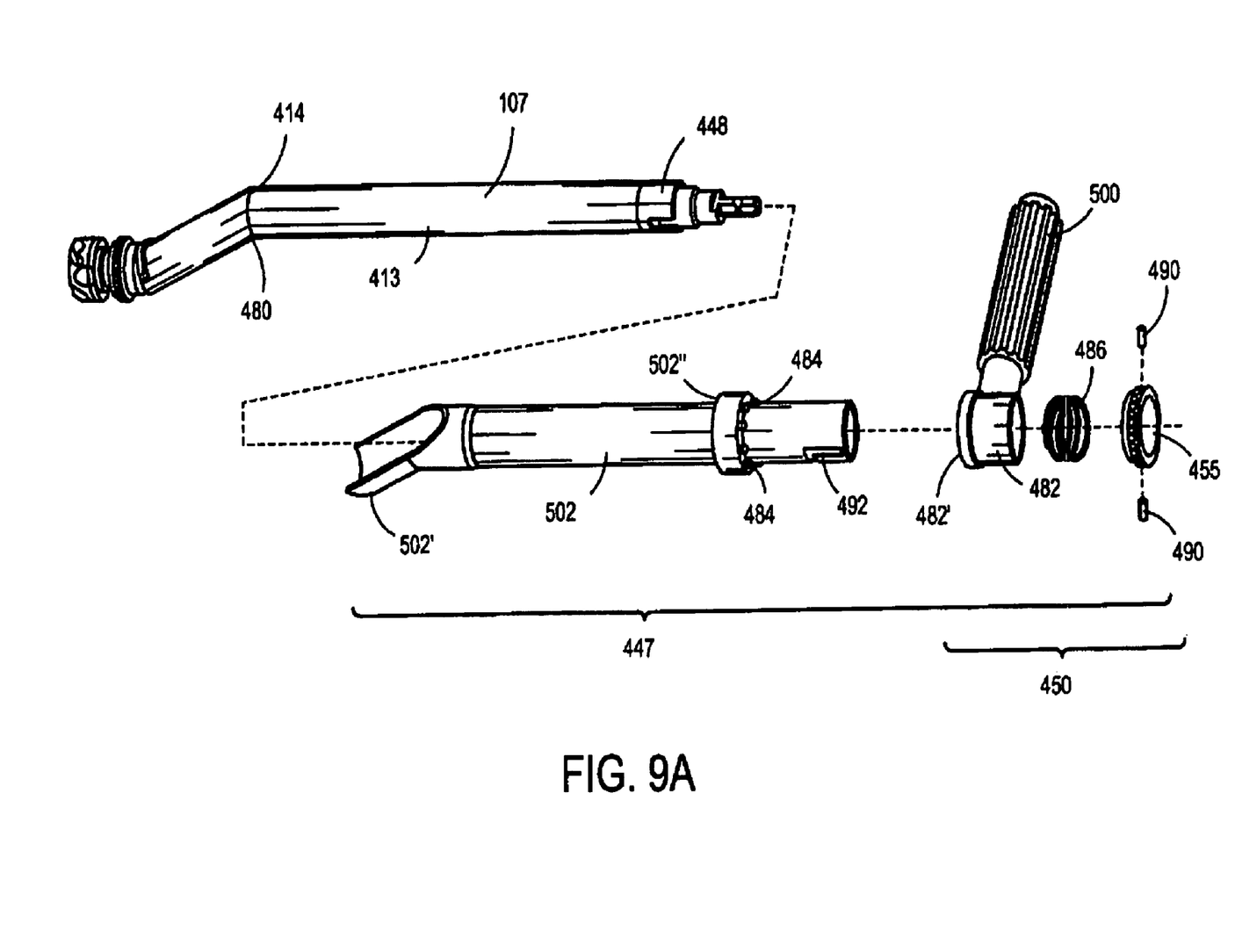
FIG. 9A is an exploded view of the alternate embodiment of FIG. 8.
Figure 9B:
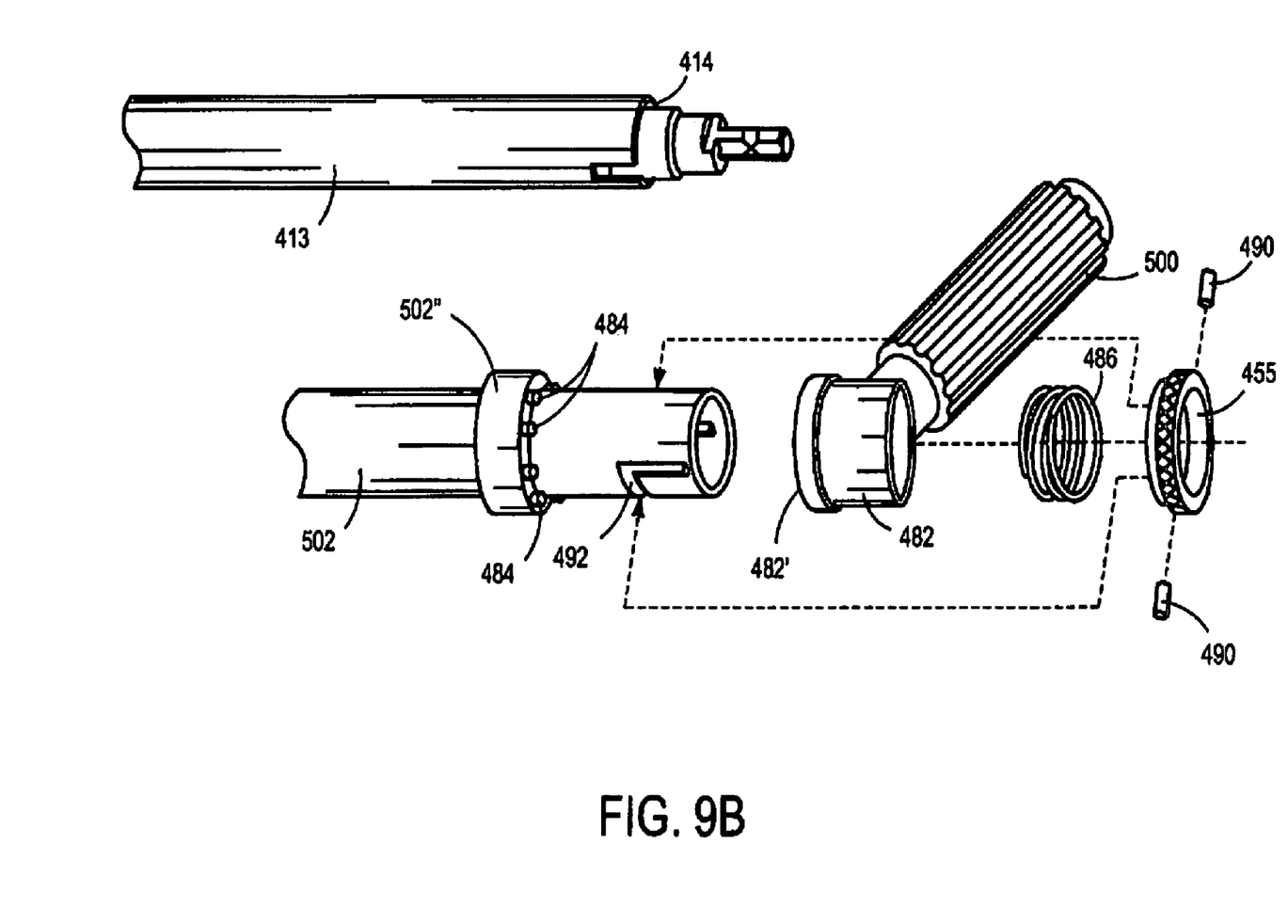
FIG. 9B is a close up of a portion of the exploded view of the alternate embodiment of FIG. 8.
Figure 9C:
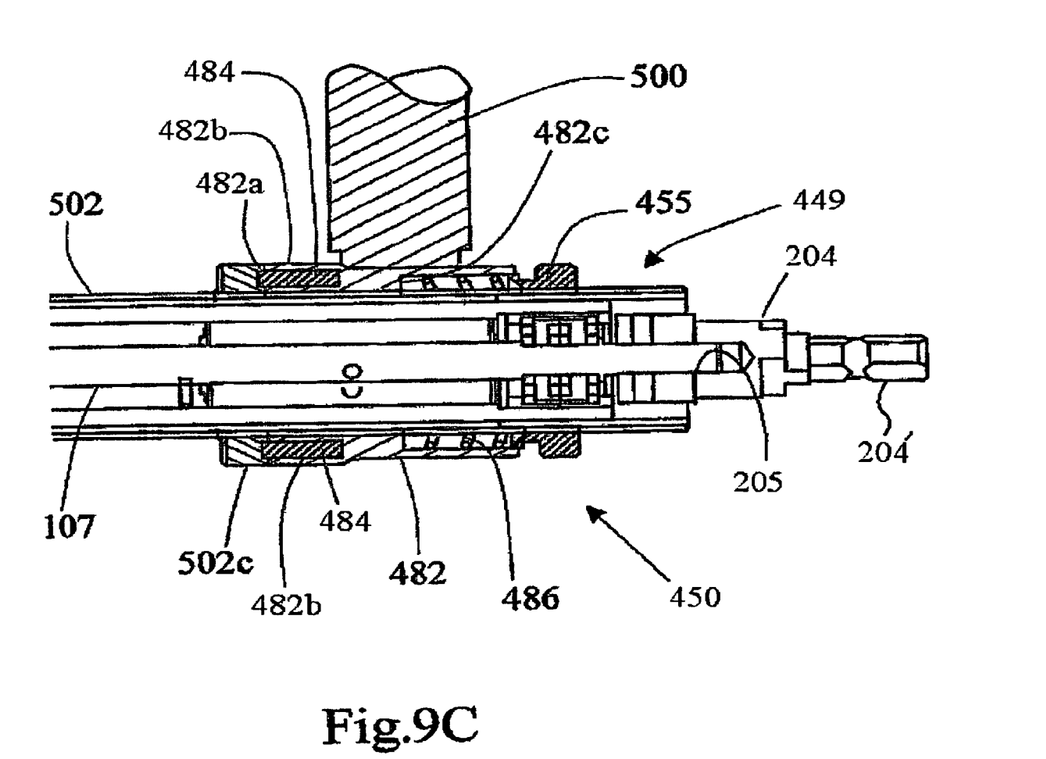
FIG. 9C is a cross-sectional view of the adjustable handle portion of the alternate embodiment of FIG. 8.
Figure 10:
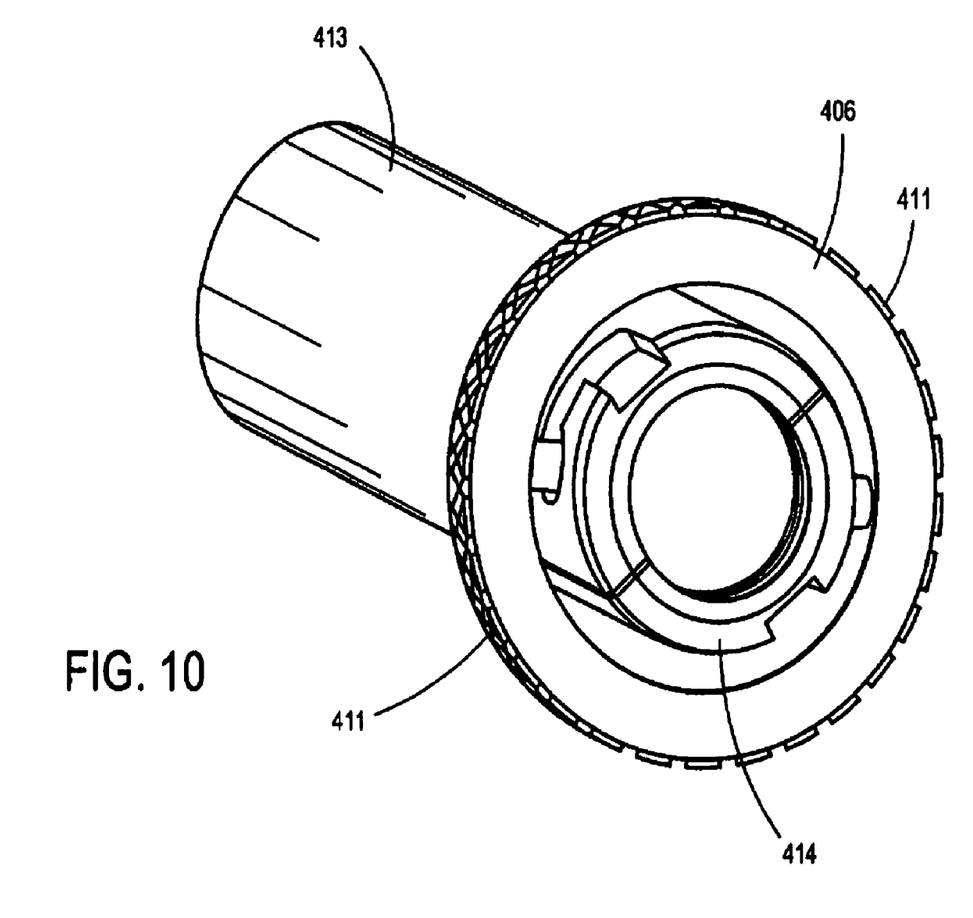
FIG. 10 is a perspective view of key components of the alternate embodiment of FIG. 8.

FIGS. 9A, 9B and 9C more clearly show how the housing members 413 and 414 are aligned and locked in place. The housing members 413 and 414 are oriented with respect to each other when a locking sleeve 502a (having an internal diameter larger than the outside diameter of the housing members) slides over them, abutting against a bend 480 in the housing members. Thin, annular Teflon sleeves (not shown) are disposed between the housing members 413 and 414 and the locking sleeve 502a to facilitate disassembly. A forward mouth section 502b of the locking sleeve 502a cradles the bend 480 of the housing members 413 and 414 so as to prevent relative rotation of the locking sleeve and housing members. At the front 448, the capture mechanism 447 has a locking device 450 which includes an annular sleeve 482 onto which the handle 500 is affixed. The sleeve 482a includes a face 482b having recesses 482c (shown in FIG. 9C) into which pins 484, fixed to a shoulder 502c of the locking sleeve 502, are received in order to torsionally rigidly hold the handle 500 in any one of eight positions, according to the preference of the surgeon. A spring 486 biases the annular sleeve 482a into engagement with the pins 484 via, on the one hand, applying spring pressure against an internal shoulder 482c (shown in FIG. 9C) in the annular sleeve 482a and, on the other hand, reacting against a locking ring 455. The locking ring 455 includes pins 490 which are affixed thereto and which enter into bayonet slots 492 in the locking sleeve 502 in order to hold the locking device 450 on the end of the locking sleeve and thus the capture mechanism 447 together. The housing members 413 and 414 are held together via the pins 490 which engage the bayonet slots 492 in each of the housing members 413 and 414 (best shown in FIG. 10 in which the annular sleeve 502, the spring 486 and the locking sleeve 502 are removed for clarity). The pins 490 of the locking ring 455 and a catch 260 interact with one another to retain the housing members 413 and 414 in a closed fashion while concurrently biasing the spring 486 so as to engage the annular sleeve 482a (and thus the handle 500) with the pins 484. Further, sufficient play in the axial movement of the annular sleeve 482a is permitted to enable the surgeon to selectively disengage the sleeve from the pins 484 so as to reposition the handle about the locking sleeve 502a in any one of the eight angular positions of the handle 500, while avoiding disassembly of the spindle 115.

Figure 11:
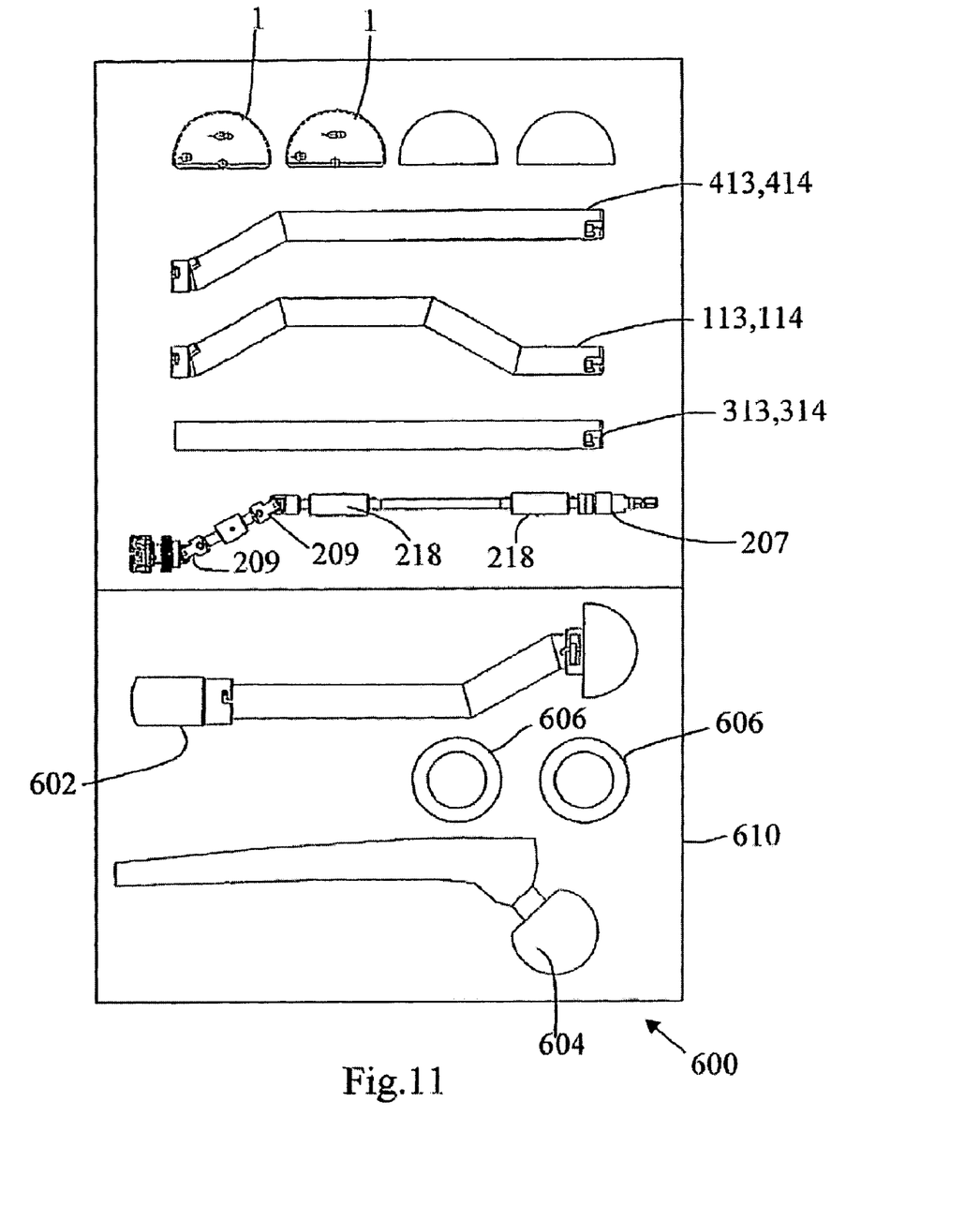
FIG. 11 is a plan view of a surgical reamer kit of the invention.

Referring now to FIG. 11, collectively, these different types of housing members 213-214, 313-314, and 413-414 can be offered as a kit 600 having a selection of different sized reamer housings 113 together with an impactor 602, acetabular implants (not shown), femoral hip prostheses 604, and acetabular cup prostheses (606), the selection of different reamer housing configurations allowing the surgeon to select between a bent, offset configuration or a straight configuration of the reamer spindle 115, 215, and 315 depending on the surgeons approach, which may vary during the same operation or between different patients.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A surgical tool driver (15, 115), comprising: a hollow elongated outer shaft (113) having a first end and a second end, said outer shaft having means for bypassing anatomical structures in a patient, including a fixed curved portion along said outer shaft for bypassing anatomical structures in a patient between said first and second ends as said driver is positioned for use; a driven end attachment assembly (204) at one said end of said outer shaft, said driven end attachment assembly being adapted for attachment to a rotary drive source; a driving end attachment assembly (220) at the other said end of said outer shaft, said driving end attachment assembly including means for selectively engaging and disengaging a surgical tool; a flexible drive shaft (207) disposed in said outer shaft, one end of said flexible drive shaft being connected to said driven end attachment assembly, and the other end of said flexible drive shaft being connected to said driving end attachment assembly.

2. The driver of claim 1, wherein at least one of the first and second ends is retained in a drive-train-enclosing relationship by a capture mechanism (455, 490, 486, 502) comprising a locking ring (455) and an elastic device (486), the locking ring biased in a locking position by the elastic device, and further including at least two housings separable from one another approximately along a plane substantially parallel to a longitudinal axis (116) of the housing to permit cleaning and/or changing out of the housings for other housings of a different form in order to suit different surgical protocols.

3. The driver of claim 2 wherein the capture mechanism (455, 490, 486, 502) further comprises a locking sleeve (482a) to which a repositionable handle (500) is attached, wherein the elastic device (486) is disposed between the locking sleeve and the locking ring so as to bias the locking ring in a locking position and to bias the locking sleeve, and thus attached repositionable handle, into a locked angular position about an axis (116) of the spindle, the locking ring aiding in holding a reamer spindle together, wherein removal of the locking ring against an elastic bias of the elastic means unfastens an end of the assembly in order to facilitate disassembly and/or cleaning.

4. The driver spindle of claim 3, wherein the locking sleeve (482a) has recesses (482c) for receiving pins (484) engaged in a shoulder (502c) fixed to the housing, the locking sleeve, and thus the adjustable handle (500), locking when the pins are received into the recesses, thereby locking the locking sleeve to the shoulder and thus to the housing.

5. The driver spindle of claim 2, wherein the locking ring (455) has at least one pin (411) affixed thereto, the at least one pin locking the locking ring in a locking position when the locking ring is biased into a bayonet recess (260, 492) by the elastic device (486).

6. The driver of claim 2, wherein the drive train (207) is selected from a group of drive trains consisting of nickel titanium drive trains, ferrous metal drive trains, flexible round wound cable drive trains, flat wire wound cable drive trains, gear-driven shaft drive trains, and drive trains having shafts connected via universal joints.

7. The driver of claim 1, said driven end attachment assembly (104, 204) and said driving end attachment assembly (120, 220) disposed in substantial linear alignment.

8. The driver of claim 1, said outer shaft (113, 413) having a collar (218'), and said driven end attachment assembly (104, 204) including a shaft (104', 204') adapted for attachment to a drive source, said shaft journaled in bearings (218) in said collar (218').

9. The driver of claim 8, said shaft (104', 204') of said driven end attachment assembly (104, 204) and said driving end attachment assembly (120, 220) disposed in substantial linear alignment.

10. The driver of claim 8, said shaft (104', 204') of said driven end attachment assembly (104, 204) having a hollow end (205), and said flexible drive shaft (107, 207) being secured in said hollow end.

11. A driver (15, 115), comprising: a hollow elongated outer shaft (113) having a first end and a second end, said outer shaft having a fixed curved portion between said first end and said second end, said fixed curved portion adapted and arranged along said outer shaft for bypassing anatomical structures in a patient between said first and second ends as said driver is positioned for use; a driven end attachment assembly (204) at one said end of said outer shaft, said driven end attachment assembly being adapted for attachment to a rotary drive source; a driving end attachment assembly (220) at the other said end of said outer shaft, said driving end attachment assembly adapted for selectively engaging and disengaging a surgical tool; a flexible drive shaft (207) disposed in said outer shaft, one end of said flexible drive shaft being connected to said driven end attachment assembly, and the other end of said flexible drive shaft being connected to said driving end attachment assembly; said outer shaft (113) having a collar (218'), and said driven end attachment assembly (204) including a shaft adapted for attachment to a drive source (204), said shaft journaled in bearings (218) in said collar; and said driving end attachment assembly (220) including a universal joint (209) drivingly connected to said flexible drive shaft.

12. The driver of claim 11, wherein at least one of the first and second ends is retained in a drive-train-enclosing relationship by a capture mechanism (455, 490, 486, 502) comprising a locking ring (455) and an elastic device (486), the locking ring biased in a locking position by the elastic device, and further including at least two housings being separable from one another approximately along a plane substantially parallel to a longitudinal axis (116) of the housing to permit cleaning and/or changing out of the housings for other housings of a different form in order to suit different surgical protocols.

13. The driver of claim 12 wherein the capture mechanism (455, 490, 486, 502) further comprises a locking sleeve (482a) to which a repositionable handle (500) is attached, wherein the elastic device (486) is disposed between the locking sleeve and the locking ring so as to bias the locking ring in a locking position and to bias the locking sleeve, and thus attached repositionable handle, into a locked angular position about an axis (116) of the spindle, the locking ring aiding in holding a reamer spindle together, wherein removal of the locking ring against an elastic bias of the elastic means unfastens an end of the assembly in order to facilitate disassembly and/or cleaning.

14. The driver spindle of claim 13, wherein the locking sleeve (482a) has recesses (482c) for receiving pins (484) engaged in a shoulder (502c) fixed to the housing, the locking sleeve, and thus the adjustable handle (500), locking when the pins are received into the recesses, thereby locking the locking sleeve to the shoulder and thus to the housing.

15. The driver spindle of claim 12, wherein the locking ring (455) has at least one pin (411) affixed thereto, the at least one pin locking the locking ring in a locking position when the locking ring is biased into a bayonet recess (260, 492) by the elastic device (486).

16. The driver of claim 12, wherein the drive train (207) is selected from a group of drive trains consisting of nickel titanium drive trains, ferrous metal drive trains, flexible round wound cable drive trains, flat wire wound cable drive trains, gear-driven shaft drive trains, and drive trains having shafts connected via universal joints.

17. The driver of claim 11, said driven end attachment assembly (104, 204) and said driving end attachment assembly (120, 220) disposed in substantial linear alignment.

18. The surgical tool, driver of claim 11, said shaft (104', 204') of said driven end attachment assembly (104, 204) having a hollow end (205), and said flexible drive shaft (107, 207) being secured in said hollow end (205).

19. The surgical tool driver of claim 18, said shaft (104', 204') of said driven end attachment assembly (104, 204) and said driving end attachment assembly (120, 220) disposed in substantial linear alignment.

20. A driver (15, 115) for an acetabular reamer, comprising:
a hollow elongated outer shaft (113) having a first end and a second end, said outer shaft having means for bypassing anatomical structures in a patient, including a fixed curved portion along said outer shaft for bypassing anatomical structures in a patient between said first and second ends as said driver is positioned for use;
a driven end attachment assembly (204) at one said end of said outer shaft, said driven end attachment assembly including means for attachment to a rotary drive source; a driving end attachment assembly (220) at the other said end of said outer shaft, said driving end attachment assembly including means for selectively engaging and disengaging an acetabular reamer; and
a flexible drive shaft (207) disposed in said outer shaft (113), one end of said flexible drive shaft being connected to said driven end attachment assembly (204), and the other end of said flexible drive shaft being connected to said driving end attachment assembly (220).

21. The driver of claim 20, wherein at least one of the first and second ends is retained in a drive-train-enclosing relationship by a capture mechanism (455, 490, 486, 502) comprising a locking ring (455) and an elastic device (486), the locking ring biased in a locking position by the elastic device, and further including at least two housings being separable from one another approximately along a plane substantially parallel to a longitudinal axis (116) of the housing to permit cleaning and/or changing out of the housings for other housings of a different form in order to suit different surgical protocols.

22. The driver of claim 21 wherein the capture mechanism (455, 490, 486, 502) further comprises a locking sleeve (482a) to which a repositionable handle (500) is attached, wherein the elastic device (486) is disposed between the locking sleeve and the locking ring so as to bias the locking ring in a locking position and to bias the locking sleeve, and thus attached repositionable handle, into a locked angular position about an axis (116) of the spindle, the locking ring aiding in holding a reamer spindle together, wherein removal of the locking ring against an elastic bias of the elastic means unfastens an end of the assembly in order to facilitate disassembly and/or cleaning.

23. The driver spindle of claim 22, wherein the locking sleeve (482a) has recesses (482c) for receiving pins (484) engaged in a shoulder (502c) fixed to the housing, the locking sleeve, and thus the adjustable handle (500), locking when the pins are received into the recesses, thereby locking the locking sleeve to the shoulder and thus to the housing.

24. The driver spindle of claim 21, wherein the locking ring (455) has at least one pin (411) affixed thereto, the at least one pin locking the locking ring in a locking position when the locking ring is biased into a bayonet recess (260, 492) by the elastic device (486).

25. The driver of claim 21, wherein the drive train (207) is selected from a group of drive trains consisting of nickel titanium drive trains, ferrous metal drive trains, flexible round wound cable drive trains, flat wire wound cable drive trains, gear-driven shaft drive trains, and drive trains having shafts connected via universal joints.

26. The driver of claim 20, wherein the hollow elongated outer shaft (113, 413) has a shaft axis (116) and the first end and the second end are situated along an axis parallel to the shaft axis (116).

27. The driver of claim 20, wherein the driving end attachment assembly (120, 220) includes a universal joint (209) connected to said flexible drive shaft (107, 207).

28. The driver of claim 27, said driven end attachment assembly (104, 204) including a shaft (104', 204'), and said outer shaft (113, 213) having a collar (218') for rotatably receiving said shaft (104', 204') of said driven end attachment assembly (120, 220).

29. The driver of claim 28, said shaft (104', 204') of said driven end attachment assembly (104, 204) having a hollow end (205), and said flexible drive shaft (107, 207) having an end thereof secured in said hollow end (205).

30. The driver of claim 29, said shaft (104', 204') of said driven end attachment assembly (104, 204) being in substantially linear alignment with said driving end attachment assembly (120, 220).

31. An apparatus to practice a method for surgically preparing a bone, comprising: means for providing a surgical tool driver with a driven end attachment assembling (104, 204) and a driving end attachment assembly (120, 220), and a curved shaft assembly (115, 215, 315) there between, said curved shaft assembly (115, 215, 315) including a rigid hollow outer shaft (113, 213, 413) and a flexible drive shaft (107, 207) in said outer shaft (113, 213, 413), said flexible drive shaft (107, 207) connected to said driven end attachment assembling (104, 204) and said driving end attachment assembly (120, 220); means for providing a surgical tool for machining a surface of the bone; means (210) for attaching the surgical tool to the driving end attachment assembly (120, 220); means for connecting the driven end attachment assembly (104, 204) to a rotary drive source; means for inserting the surgical tool through a surgical wound (113, 213, 413); means for positioning the surgical tool (500) against a bone surface while positioning the curved portion of the shaft assembly (113, 213, 413) around intervening anatomy; and means (104, 204) for driving the tool to machine the bone surface.

* * * * *